US012797555B2

(12) United States Patent
Rivier

(10) Patent No.: US 12,797,555 B2
(45) Date of Patent: Nov. 17, 2026

(54) NEEDLE SHIELD ASSEMBLY FOR A SYRINGE

(71) Applicant: Becton Dickinson France, Le Pont-de-Claix (FR)

(72) Inventor: Cédric Rivier, Voreppe (FR)

(73) Assignee: Becton Dickinson France, Le Pont-de-Claix (FR)

( * ) Notice: Subject to any disclaimer, the term of this patent is extended or adjusted under 35 U.S.C. 154(b) by 447 days.

(21) Appl. No.: 18/563,605

(22) PCT Filed: May 24, 2022

(86) PCT No.: PCT/EP2022/064057

§ 371 (c)(1),
(2) Date: Nov. 22, 2023

(87) PCT Pub. No.: WO2022/248474

PCT Pub. Date: Dec. 1, 2022

(65) Prior Publication Data

US 2024/0269392 A1 Aug. 15, 2024

(30) Foreign Application Priority Data

May 26, 2021 (EP) ..................................... 21305692

(51) Int. Cl.
*A61M 5/32* (2006.01)
*A61M 5/31* (2006.01)

(52) U.S. Cl.
CPC ........ *A61M 5/3202* (2013.01); *A61M 5/3213* (2013.01); *A61M 2005/3107* (2013.01); (Continued)

(58) Field of Classification Search
CPC .............. A61M 5/3202; A61M 5/3213; A61M 2005/3107; A61M 2005/312; (Continued)

(56) References Cited

U.S. PATENT DOCUMENTS 5,746,733 A * 5/1998 Capaccio ............ A61M 5/3202 604/240
5,858,008 A * 1/1999 Capaccio ............ A61M 5/3213 604/263

(Continued)

FOREIGN PATENT DOCUMENTS

CN 109414551 A 3/2019
EP 3047868 A1 7/2016

(Continued)

*Primary Examiner* — Tasnim Mehjabin Ahmed
(74) *Attorney, Agent, or Firm* — The Webb Law Firm

(57) ABSTRACT

The present invention relates to a needle shield assembly for a medical injection device such as a syringe including at its distal end a longitudinal hub portion equipped with a needle on which said needle shield assembly is intended to be removably engaged, the said needle shield assembly including a rigid shield elongated in an longitudinal direction formed of a first material, said rigid shield having a wall including an inner surface and an outer surface, a flexible shield formed of a second material different from the first material, said flexible shield including an outer layer having an inner surface covering at least part of the rigid shield outer surface and an inner layer, being capable of receiving in a sealing way at least part of the hub portion of the medical injection device, and covering at least partly the inner surface of the rigid shield and a septum formed of a third material different from the said first and second materials, said septum being at least partly in contact with the inner surface of the rigid shield and being capable of ensuring a fluid and tight seal of the distal end of the medical injection device.

15 Claims, 2 Drawing Sheets

(52) U.S. Cl.
CPC ................. *A61M 2005/312* (2013.01); *A61M 2205/3569* (2013.01); *A61M 2205/58* (2013.01); *A61M 2207/10* (2013.01)

(58) Field of Classification Search
CPC ...... A61M 2205/3569; A61M 2205/58; A61M 2207/10
See application file for complete search history.

(56) References Cited

U.S. PATENT DOCUMENTS

| | | | | |
|---|---|---|---|---|
| 10,166,342 | B2 | 1/2019 | Protasiewicz et al. | |
| 10,953,161 | B2 | 3/2021 | Lanzi et al. | |
| 2005/0038391 | A1 | 2/2005 | Wittland et al. | |
| 2014/0288503 | A1 * | 9/2014 | Julian | A61M 5/321 29/428 |
| 2016/0206829 | A1 * | 7/2016 | Protasiewicz | A61M 5/3204 |
| 2019/0217018 | A1 | 7/2019 | Bauss et al. | |
| 2019/0328485 | A1 * | 10/2019 | Bauss | A61B 90/98 |
| 2021/0379294 | A1 | 12/2021 | Pouget et al. | |

FOREIGN PATENT DOCUMENTS

| | | | |
|---|---|---|---|
| EP | 3202448 | A1 | 8/2017 |
| JP | 2014506493 | A | 3/2014 |
| JP | 2019504695 | A | 2/2019 |
| JP | 2019520178 | A | 7/2019 |
| WO | WO2012103141 | A1 | 8/2012 |
| WO | 2020083842 | A1 | 4/2020 |

* cited by examiner

NEEDLE SHIELD ASSEMBLY FOR A SYRINGE

CROSS-REFERENCE TO RELATED APPLICATIONS

This application is the United States national phase of International Application No. PCT/EP2022/064057 filed May 24, 2022, and claims priority to European Patent Application No. 21305692.2 filed May 26, 2021, the disclosures of which are hereby incorporated by reference in their entireties.

BACKGROUND OF THE INVENTION

Field of the Invention

The present invention relates to a needle shield assembly for a medical injection device for covering a needle attached thereon, a medical injection device comprising said needle shield assembly and a method for manufacturing said needle shield assembly. The invention is particularly well suited for the healthcare industry.

Description of Related Art

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to a medical container of the invention, and the "proximal direction" is to be understood as meaning the opposite direction to said direction of injection, that is to say the direction towards the user's hand holding a container as for an injection operation.

Medical injection devices, for example pre-fillable or prefilled syringes, usually comprise a hollow body or barrel forming a container for a medical product or a medical composition. The body comprises a distal end, optionally provided with a needle, and a proximal end, usually provided with a flange. The distal end of the body is typically in the form of a longitudinal tip defining a fluid path through which the medical solution is expelled from the hollow body.

When the medical injection device is provided with a needle, and in order to prevent any injury prior to final use, a needle shield assembly is mounted on the tip so as to enclose the needle. This renders the needle physically inaccessible by the persons around the device. The needle shield assembly usually comprises an inner needle shield, in a material with elastomeric properties, and may further comprise an outer needle shield, in rigid plastic, surrounding the inner needle shield.

The inner needle shield ensures the sealing of the medical injection device. To that purpose, the inner needle shield comprises a sealing portion that sealingly contacts the outer surface of the syringe's tip to provide a tight seal. The inner needle shield prevents any contamination of the medical composition from the outside environment, thereby assuring the container closure integrity. The inner needle shield further prevents any leakage of composition from the outlet of the needle to the external environment. To that purpose, the needle is preferably pricked in the inner needle shield.

The outer needle shield typically surrounds the inner needle shield and provides a rigid protection to the needle, helping maintaining its integrity during transport and/or storage.

A drawback of the known needle shield assembly is that it may be relatively difficult to remove them from the tip. In order to do so, the user has to grip both the injection device and the needle shield assembly, and pull the shield assembly by exerting an effort which may be quite important.

The force needed to remove a needle shield assembly is measured by a physical parameter commonly known as "pull out force". The pull out force necessary for removing the known needle covers from an injection device, such as a syringe, may be quite high.

As a consequence, a user having a reduced strength, for example weakened by a disease, may not be able to remove the needle shield and use the injection device for his. Depending on the medical composition stored in the medical injection device, it is known to adapt the composition of the inner needle shield made of a material with elastomeric properties. Indeed, the medical composition may react differently depending on the composition of the inner needle shield. The aim is thus to select an inner needle shield composition that does not react with the medical composition. Additionally, it is also necessary to adapt the material of the outer needle shield depending on the composition of the inner needle shield. Indeed, all the materials are not compatible leading to a wide number of needle shield assemblies to produce, each range of needle shield assemblies including one specific inner needle shield composition and one specific outer needle shield composition, both compositions being compatibles. Additionally, the different inner needle shield compositions and therefore the ranges of needle shield assemblies, do not have the same pull out force. Thus, the pull out force is not repeatable and this can be disconcerting for a user.

There is therefore a need for a needle shield assembly showing a constant pull-out force whatever the formulation of the medical product contained in the barrel, reducing the need to produce a wide range of needle shield assemblies, and ensuring constant needle shield properties such as leaks.

SUMMARY OF THE INVENTION

A first aspect of the present invention is a needle shield assembly for a medical injection device such as a syringe comprising at its distal end a longitudinal hub portion equipped with a needle on which said needle shield assembly is intended to be removably engaged, the said needle shield assembly comprising:

- A rigid shield elongated in a longitudinal direction formed of a first material, said rigid shield having a wall including an inner surface and an outer surface,
- a flexible shield formed of a second material different from the first material, said flexible shield comprising an outer layer having an inner surface covering at least part of the rigid shield outer surface and an inner layer, being capable of receiving in a sealing way at least part of the hub portion of the medical injection device, and covering at least partly the inner surface of the rigid shield and
- a septum formed of a third material different from the said first and second materials, said septum being at least partly in contact with the inner surface of the rigid shield and being capable of ensuring a fluid and tight seal of the distal end of the medical injection device.

Without willing to be bound by a theory, it is believed that the needle shield according to the present invention allows a constant pull-out force without requiring to adapt the flexible shield to the medical composition stored in the medical injection device. Indeed, in the needle shield assembly according to the present invention, only the composition of the septum is adapted to the medical composition. Thus, the pull-out force is repeatable. Moreover, the needle shield assembly is hermetic preventing the risk of leaks. There is no risk that the medical composition escapes from the needle. Additionally, the barrel integrity of the medical injection device remains intact. There is no risk that impurities contaminate the medical composition present in the barrel of the medical injection device. Furthermore, in the prior art, it is known that the external part of the needle shield assembly is made of a rigid material, optionally having a gripping part which may irritate the fingers of the user after repeated injections, i.e. repeated removal of needle shield assembly. On the contrary, in the present invention, the external part of the needle shield assembly is made of flexible material offering a soft touch to the user. The rigidity of the needle shield assembly of the invention facilitates its gripping. The needle shield assembly may easily be removed without any risk of bending the needle.

In one embodiment, the needle shield assembly further comprises an annular bridge linking the inner layer and the outer layer of the flexible shield at the proximal open end. In this embodiment, the sealing between the flexible shield and the rigid shield is optimized.

In another embodiment, the inner and the outer layers of the flexible shield are separated by the rigid shield wall. In one embodiment, the wall of the rigid shield comprises a first portion located at the distal end of the needle shield assembly and a second portion being located at the proximal end of the needle shield assembly, said first portion comprising a first cavity capable of receiving the septum and said second portion comprising a second cavity capable of receiving the inner layer of the flexible shield.

In one embodiment, the inner surface of the outer layer of the flexible surrounds the first portion of the wall of the rigid shield and optionally the second portion of the wall of the rigid shield.

In one embodiment, the rigid shield comprises at the proximal end of the needle shield assembly a circular groove.

Additionally, a ring seal may be located on the flexible shield and configured to fit in the circular groove of the rigid shield. Preferably, the ring seal is made of rubber or Thermo Plastic Elastomer (TPE). In this embodiment, there is no risk that the syringe is removed accidently from the needle shield assembly.

In one embodiment, the flexible shield comprises at the proximal end of the needle shield ribs configured to receive recesses located on an outer surface of the hub portion of the medical injection device. In this embodiment, the syringe is well engaged in the needle shield assembly.

Preferably, the first material is a thermoplastic. The first material may be polypropylene (PP), polyethylene (PE), polyethylene terephthalate (PET), polystyrene (PS) or polycarbonate (PC). Preferably, the second material is a deformable material, made of a material having elastomeric properties, such as Thermo Plastic Elastomer (TPE).

Advantageously, the first material is PP and the second material is TPE. In this embodiment, it is believed that a specific chemical bond is realized between both materials. Thus, the flexible shield is firmly attached to the rigid shield.

Preferably, the third material is a rubber, such as a butyl rubber.

In one embodiment, a wireless transmitter is located between the rigid shield and the flexible shield. The wireless transmitter may be a Radio Frequency Identification tag, a ultra wide-band real-time location system (RTLS), a wifi real-time load forecasting (RTLF), an infrared RTLS.

Preferably, the wireless transmitter is a Radio Frequency Identification (RFID) tag located between the rigid shield and the flexible shield, said RFID tag comprising at least one RFID antenna. In this embodiment, it is believed that the needle shield assembly of the invention allows individual traceability of each medical injection device from the manufacturing process to the final use of the medical injection device. Besides, the RFID tag is well protected from removal or external damage that may occur during the packaging, storing, distribution of the medical injection device. Furthermore, the RFID tag being concealed between the rigid shield and the flexible shield of the needle shield assembly, there is no visual impact. Additionally, the insertion of the RFID tag has only a limited impact on the manufacturing process.

In one embodiment, the RFID tag does not comprise a chip. Such chipless RFID tag does not require a chip to be read by a reader.

In one embodiment, a chip is connected to the at least one RFID antenna.

In one embodiment, the RFID tag is a Low Frequency Radio Frequency Identification (LF-RFID) tag. Low frequencies are usually about 30 KHz to 300 KHz. In this embodiment, a RFID reader can for example read the LF-RFID tag at a distance up to about ten cm.

In one embodiment, the RFID tag is a High Frequency Radio Frequency Identification (HF-RFID) tag. High frequencies are usually about 1-15 MHZ. In this embodiment, a RFID reader can for example read the HF-RFID tag at a distance about one meter.

In one embodiment, the RFID tag is a High-Frequency Near Field Communication (HF-NFC) tag. The frequencies are usually about 13.56 MHz. In this embodiment, a NFC reader can for example read the HF-NFC tag at a distance up to a few centimeters. HF-NFC differs from HF-RFID in that it can be read by a NFC smartphone. In one embodiment, the RFID tag is a double frequency tag including simultaneously a HF-NFC and an UHF RFID. For example, it can be read with both a NFC smartphone or an UHF reader.

Preferably, the RFID tag is an Ultra High Frequency Radio Frequency Identification (UHF-RFID) tag. Ultra high frequencies are usually about 400-1000 MHz. In this embodiment, a RFID reader can for example read the UHF-RFID tag at a distance about fifteen meters.

In one embodiment, the wireless transmitter is in contact with the outer surface of the wall of the rigid shield and is surrounded by the inner surface of the outer layer of the flexible shield.

Preferably, the wireless transmitter is in contact with the outer surface of the wall of the rigid shield and is surrounded by the inner surface of the outer layer of the flexible shield.

Preferably, the RFID tag has a width extending between 10% and 100% of the circumference of the outer surface of the rigid shield, 100% being excluded, and advantageously between 40% and 100%, more preferably between 50 and 100%, or between 50 to 100% and advantageously between 50% and 90% of the circumference of the outer surface of the rigid shield. In this embodiment, it is believed that the data transmission level to the RFID reader is improved.

Advantageously, the RFID tag has a length extending strictly less than 100% of a length of the needle shield assembly. Preferably, the RFID tag has a length extending over at least 15%, more preferably 25%, of a length of the needle shield assembly. It is believed that the length of the tag can have an impact on the data transmission level of the RFID tag to the RFID reader.

In one embodiment, the rigid shield comprises grooves configured to receive a part of the wireless transmitter, in particular a part of the RFID tag. In this embodiment, it is believed that the grooves increases the sealing of the wireless transmitter, in particular a part of the RFID tag so that there is no risk that the wireless transmitter, in particular a part of the RFID tag falls during the manufacturing process.

A second aspect of the present invention is a medical device comprising at its distal end a longitudinal hub portion equipped with a needle and a needle shield assembly according to the present invention sealingly engaging the needle. Preferably, the medical injection device is a syringe.

A third aspect of the present invention is a method for manufacturing a needle shield assembly according to anyone of the preceding claims, comprising:

A. Providing a rigid shield elongated in a longitudinal direction formed of a first material, said rigid shield having a wall including an inner surface and an outer surface, B. Implementing a flexible shield formed of a second material different from the first material onto the rigid shield, said flexible shield comprising an outer layer configured to cover at least part of the rigid shield outer surface and an inner layer, and configured to cover at least partly the inner surface of the rigid shield and C. Inserting a septum within the rigid shield, said septum being formed of a third material different from the said first and second materials, said septum being configured to be at least partly in contact with the inner surface of the rigid shield.

In one embodiment, in step A), the rigid shield is injection molded, and the method comprises a step D) performed before step A) wherein a wireless transmitter is disposed in a mold before the injection molding of the rigid shield In another embodiment, in step A), the rigid shield is injection molded, and the method comprises a step D) performed after step A) wherein a wireless transmitter is overmolded on the outer surface of the wall of the rigid shield before being surrounded by the outer layer of the flexible shield.

In one embodiment, in step B), the flexible shield is implemented on the rigid shield by overmolding. In one embodiment, steps A) and B) are performed simultaneously for example by injection molding, in particular by bi-injection molding process.

In step C), the septum is snap fitted inside the rigid shield.

In one embodiment, the method further comprises a step E) performed after step A) wherein a ring seal is overmolded or clipped over the rigid shield.

BRIEF DESCRIPTION OF THE DRAWINGS

The terms Fig., Figs., Figure, and Figures are used interchangeably in the specification to refer to the corresponding figures in the drawings.

The invention and advantages arising therefrom will clearly emerge from the detailed description that is given below with reference to the appended drawings as follows.

DESCRIPTION OF THE INVENTION

Figure 1:
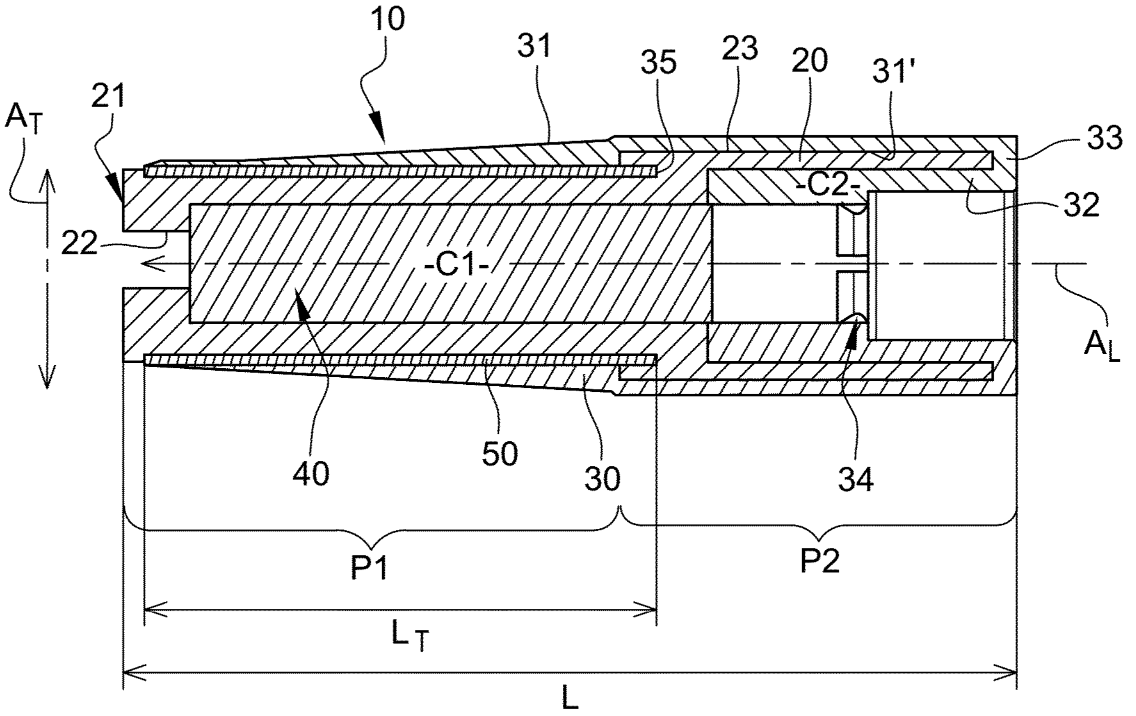
FIG. 1 is a transversal view of a needle shield assembly according to one embodiment of the invention.
Figure 2:
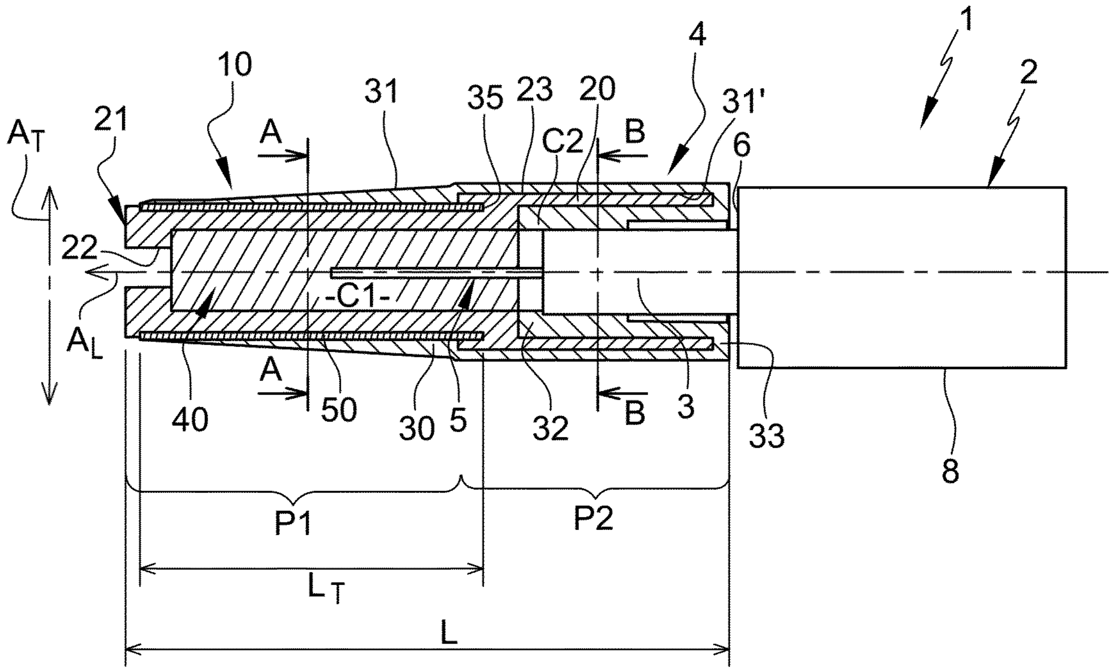
FIG. 2 is a longitudinal cross sectional view of a part of the medical injection device furnished with the needle shield assembly according to the embodiment illustrated in FIG. 1.

FIG. 1 shows a needle shield assembly 10 having a longitudinal axis $A_L$ and a transversal axis $A_T$ intended to cover a medical injection device 1 (FIG. 2).

FIG. 2 shows the medical injection device 1 such as a syringe comprising a barrel 2 having a longitudinal axis $A_L$ and a transversal axis $A_T$. Said barrel 2 comprises a side wall 8 and thus forms a reservoir, adapted to contain a medical composition to be injected.

The medical injection device or syringe 1 further comprises a longitudinal hub portion 3 provided at its distal end 4 and extending along the axis $A_L$ from the distal end of the barrel 2. The hub portion 3 is partially hollow so as to form a channel in fluidic communication with the barrel 2.

A needle 5 may be attached to the hub portion 3 of the medical injection device. For example, the needle may be glued to the hub portion 3. In particular, the needle shield assembly 10 is intended to cover the hub portion 3 of the medical injection device 1, so as to protect the needle. The medical injection device 1 can also include, at its distal end, a distal shoulder 6 which narrows with respect to the barrel 2.

The medical injection device or syringe 1 also includes a plunger rod (not shown) having a plunger (not shown) and a barrel stopper (not shown) provided at an end thereof. The plunger is caused to slidably move in the barrel 2 along an inner surface of the side wall 8 to cause the medical composition to be expelled from the barrel 2 through the needle 5. The medical composition comprised in the medical injection device 1 may be for example, a liquid medicament, a drug or a pharmaceutical composition such as a vaccine.

As illustrated in FIGS. 1-2, the needle shield assembly 10 comprises a rigid shield 20 elongated in an longitudinal direction along longitudinal axis $A_L$, said rigid shield 20 having a wall 21 including an inner surface 22 and an outer surface 23. The rigid shield is typically made of rigid material. Preferably, the rigid shield 20 is made of polypropylene (PP), polyethylene (PE), polyethylene terephthalate (PET), polystyrene (PS) or polycarbonate (PC), much preferably of polypropylene. The rigid shield 20 can be manufactured by injection molding.

The needle shield assembly 10 further comprises a flexible shield 30, said flexible shield 30 comprising an outer layer 31 covering at least part of the rigid shield outer surface 23 and an inner layer 32, being capable of receiving in a sealing way at least part of the hub portion 3 of the medical injection device 1, and covering at least partly the inner surface 22 of the rigid shield 20. Preferably, the flexible shield 30 is made of a deformable material such as TPE (Thermo Plastic Elastomer). The flexible shield 30 may be provided on the rigid shield 20 by overmolding.

The needle shield assembly 10 further comprises a septum 40 being at least partly in contact with the inner surface 22 of the rigid shield 20 and being capable of ensuring a fluid and tight seal of the distal end of the medical injection device 1. Preferably, the septum 40 is made of rubber, such as butyl rubber. The septum 40 may be inserted within the rigid shield 20.

According to an embodiment, the rigid shield 20 comprises an opened distal end and an opened proximal end. The flexible shield 30 may also comprise an opened distal end and an opened proximal end. Typically, the septum 50 comprises a closed distal end and an opened proximal end.

As illustrated in FIGS. 1-2, the needle shield assembly 1 further comprises an annular bridge 33 linking the inner layer 32 and the outer layer 31 of the flexible shield 30 at the proximal open end.

The wall 21 of the rigid shield 20 may comprise a first portion P1 located at the distal end of the needle shield assembly 10 and a second portion P2 being located at the proximal end of the needle shield assembly 10. The first portion P1 may comprise a first cavity C1 capable of receiving the septum 40 and said second portion P2 comprises a second cavity C2 capable of receiving the inner layer 32 of the flexible shield 30.

For example, the outer layer 31 of the flexible shield 30 has an inner surface 31' surrounding the first portion P1 and the second portion P2 of the wall 21 of the rigid shield 20.

The flexible shield 30 may comprise at the proximal end of the needle shield assembly 10 ribs 34 configured to receive recesses (not shown) located on an outer surface of the hub portion 3 of the syringe 1.

The needle shield assembly may comprise a wireless transmitter, preferably a RFID tag 50 located between the rigid shield 20 and the flexible shield 30, said RFID tag 50 comprising at least one RFID antenna (not shown). The RFID tag 50 may further comprise a chip connected to the antenna. The RFID tag 50 may be a chipless RFID tag, a LF-RFID tag, a HF-RFID tag or an UHF-RFIF tag, or a HF-NFC RFID tag.

Preferably, the RFID tag 50 is in contact with the outer surface 23 of the wall 21 of the rigid shield 20 and is surrounded by an inner surface 31' of the outer layer 31. Advantageously, the rigid shield 20 comprises grooves 35 configured to receive a part of the RFID tag 50.

Preferably, the RFID tag 50 has a width (not shown) extending between 10% and 100% of the circumference of the outer surface of the rigid shield, 100% being excluded, and advantageously between 40% and 100%, more preferably between 50 and 100%, or between 50 to 100% and advantageously between 50% and 90% of the circumference of the outer surface of the rigid shield 20. Advantageously, the RFID tag 50 has a length LT extending strictly less than 100% of a length L of the needle shield assembly 10. Preferably, the RFID tag 50 has a length Lr extending over at least 15%, more preferably 25% of a length L of the needle shield assembly 10. This enables maximizing the exposition of the antenna to electromagnetic waves of a reader.

For example, the RFID tag 50 may be disposed in a mold before the injection molding of the rigid shield 20. Alternatively, the RFID tag 50 may be overmolded on the outer surface 23 of the wall 21 of the rigid shield 20 before being surrounded by the outer layer 31 of the flexible shield 30.

Figure 3:
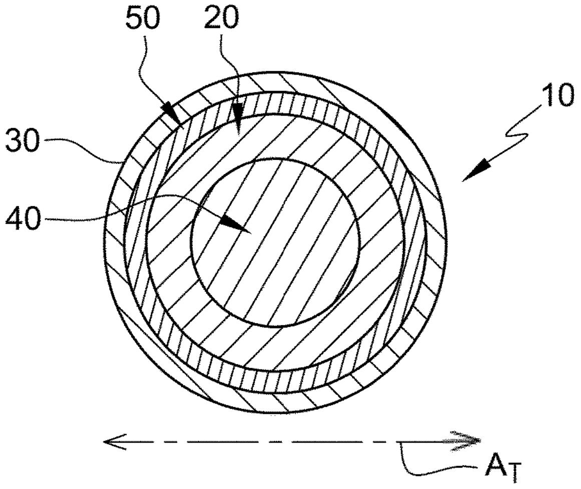
FIG. 3 is a transversal cross sectional view of the needle shield assembly according to the embodiment illustrated in FIGS. 1 and 2.
Figure 4:
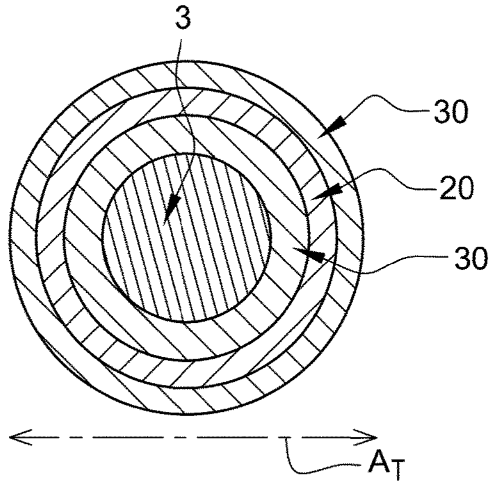
FIG. 4 is a transversal cross sectional view of the needle shield assembly according to the embodiment illustrated in FIGS. 1 and 2 and FIG. 5 is a transversal view of a needle shield assembly according to one embodiment of the invention.

FIG. 3 illustrated a cross view of the section A-A (FIG. 2) of the needle shield assembly 1 and FIG. 4 illustrated a cross view of the section B-B (FIG. 4) of the needle shield assembly 1.

Figure 5:
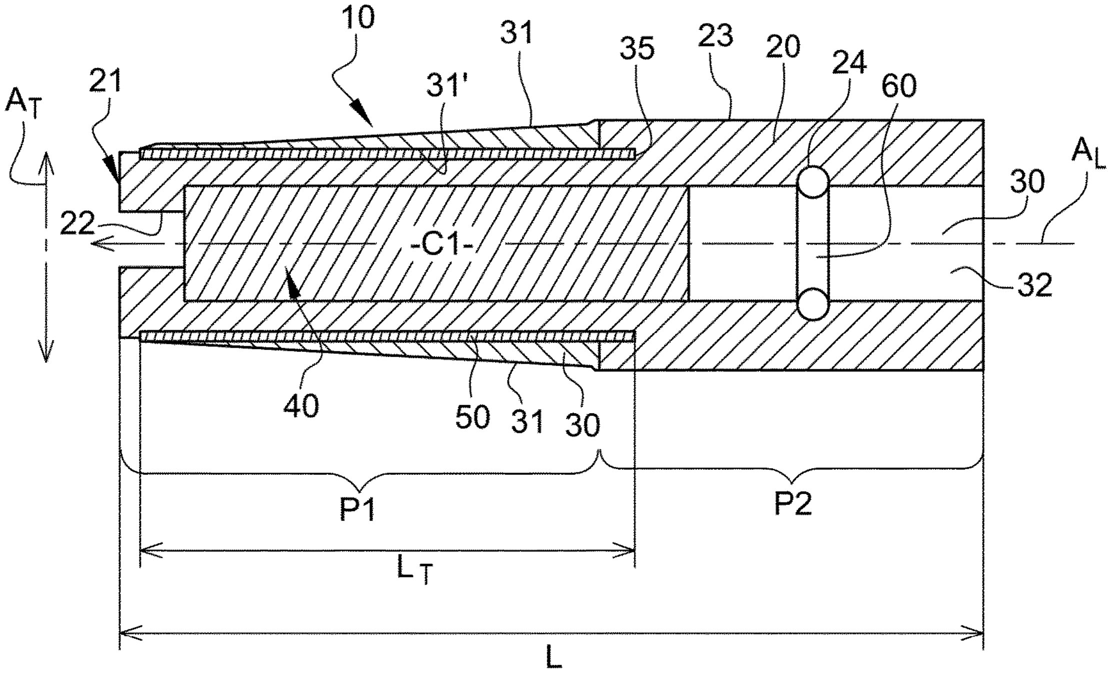

FIG. 5 shows a needle shield assembly 10 according another embodiment comprising a rigid shield 20 elongated in an longitudinal direction along longitudinal axis $A_L$, said rigid shield 20 having a wall 21 including an inner surface 22 and an outer surface 23. The rigid shield is typically made of rigid material. Preferably, the rigid shield 20 is made of polypropylene (PP), polyethylene (PE), polyethylene terephthalate (PET), polystyrene (PS) or polycarbonate (PC), much preferably of polypropylene. The rigid shield 20 can be manufactured by injection molding.

The needle shield assembly 10 further comprises a flexible shield 30, said flexible shield 30 comprising an outer layer 31 covering at least part of the rigid shield outer surface 23 and an inner layer 32, being capable of receiving in a sealing way at least part of the hub portion 3 of the medical injection device 1, and covering at least partly the inner surface 22 of the rigid shield 20. Preferably, the flexible shield 30 is made of a deformable material such as TPE (Thermo Plastic Elastomer). The flexible shield 30 may be provided on the rigid shield 20 by overmolding.

The needle shield assembly 10 further comprises a septum 40 being at least partly in contact with the inner surface 22 of the rigid shield 20 and being capable of ensuring a fluid and tight seal of the distal end of the medical injection device 1. Preferably, the septum 40 is made of rubber, such as butyl rubber. The septum 40 may be inserted within the rigid shield 20.

In this embodiment, the rigid shield 20 comprises an opened distal end and an opened proximal end, the flexible shield 30 comprises an opened distal end and an opened proximal end, and the septum 50 comprises a closed distal end and an opened proximal end.

In this example, the inner 32 and the outer 31 layers are separated by the rigid shield wall 21.

The wall 21 of the rigid shield 20 may comprise a first portion P1 located at the distal end of the needle shield assembly 10 and a second portion P2 being located at the proximal end of the needle shield assembly 10. The first portion P1 may comprise a first cavity C1 capable of receiving the septum 40 and said second portion P2 comprises a second cavity C2 capable of receiving the inner layer 32 of the flexible shield 30.

For example, the outer layer 31 of the flexible shield 30 has an inner surface 31' surrounding the first portion P1.

The flexible shield 30 may comprise at the proximal end of the needle shield assembly 10 ribs (not shown) configured to receive recesses (not shown) located on an outer surface of the hub portion 3 of the syringe 1.

Preferably, the rigid shield 20 comprises at the proximal end of the needle shield assembly 10 a circular groove 24 configured to receive a ring seal 60 surrounding the ribs of the flexible shield 30. The ring seal 60 may be overmpolder over the rigid shield. For example, the ring seal is made of rubber or TPE.

The needle shield assembly may comprise a RFID tag 50 located between the rigid shield 20 and the flexible shield 30, said RFID tag 50 comprising at least one RFID antenna (not shown). The RFID tag 50 may further comprise a chip connected to the antenna. The RFID tag 50 may be a chipless RFID tag, a LF-RFID tag, a HF-RFID tag or an UHF-RFIF tag, or a HF-NFC RFID tag.

Preferably, the RFID tag 50 in contact with the outer surface 23 of the wall 21 of the rigid shield 20 is surrounded by an inner surface 31' of the outer layer 31. Advantageously, the rigid shield 20 comprises grooves 35 configured to receive a part of the RFID tag 50.

Preferably, the RFID tag 50 has a width (not shown) extending between 10% and 100% of the circumference of the outer surface of the rigid shield, 100% being excluded, and advantageously between 40% and 100%, more preferably between 50 and 100%, or between 50 to 100% and advantageously between 50% and 90% of the circumference of the outer surface of the rigid shield 20. Advantageously, the RFID tag 50 has a length LT extending strictly less than 100% of a length L of the needle shield assembly 10.

Preferably, the RFID tag 50 has a length LT extending over at least 15%, more preferably 25% of a length L of the needle shield assembly 10. This enables maximizing the exposition of the antenna to electromagnetic waves of a reader.

For example, the RFID tag 50 may be disposed in a mold before the injection molding of the rigid shield 20. Alternatively, the RFID tag 50 may be overmolded on the outer surface 23 of the wall 21 of the rigid shield 20 before being surrounded by the outer layer 31 of the flexible shield 30.

The needle shield according to the present invention provides a soft touch to the user and offers a constant pull-out force.

The invention claimed is:

1. A needle shield assembly for a medical injection device, such as a syringe, comprising at its distal end a longitudinal hub portion equipped with a needle on which said needle shield assembly is intended to be removably engaged, the said needle shield assembly comprising:

a rigid shield elongated in a longitudinal direction formed of a first material, said rigid shield having a wall including an inner surface and an outer surface, a flexible shield formed of a second material different from the first material, said flexible shield comprising an outer layer having an inner surface covering at least part of the rigid shield outer surface and an inner layer being capable of receiving in a sealing way at least part of the hub portion of the medical injection device and of covering at least partly the inner surface of the rigid shield and a septum formed of a third material different from the said first and second materials, said septum being at least partly in contact with the inner surface of the rigid shield and being capable of ensuring a fluid and tight seal of the distal end of the medical injection device.

2. The needle shield assembly according to claim 1, wherein the needle shield assembly further comprises an annular bridge linking the inner layer and the outer layer of the flexible shield at a proximal open end of the needle shield assembly.

3. The needle shield assembly according to claim 1, wherein the inner and the outer layers are separated by the rigid shield wall.

4. The needle shield assembly according to claim 1, wherein the wall of the rigid shield comprises a first portion located at a distal end of the needle shield assembly and a second portion being located at a proximal end of the needle shield assembly, said first portion comprising a first cavity capable of receiving the septum and said second portion comprising a second cavity capable of receiving the inner layer of the flexible shield.

5. The needle shield assembly according to claim 4, wherein the inner surface of the outer layer of the flexible shield surrounds at least one of the first portion of the wall of the rigid shield and the second portion of the wall of the rigid shield.

6. The needle shield assembly according to claim 1, wherein the rigid shield comprises at a proximal end of the needle shield assembly a circular groove.

7. The needle shield assembly according to claim 6, wherein a ring seal may be located on the flexible shield and may be configured to fit in the circular groove of the rigid shield.

8. The needle shield assembly according to claim 1, wherein a wireless transmitter is located between the rigid shield and the flexible shield.

9. The needle shield assembly according to claim 8, wherein the wireless transmitter is in contact with the outer surface of the wall of the rigid shield and is surrounded by the inner surface of the outer layer of the flexible shield.

10. The needle shield assembly according to claim 9, wherein the rigid shield comprises grooves configured to receive a part of the wireless transmitter.

11. A medical injection device comprising at its distal end a longitudinal hub portion equipped with a needle and a needle shield assembly according to claim 1 sealingly engaging the needle.

12. A method for manufacturing a needle shield assembly, comprising:

A. providing a rigid shield elongated in a longitudinal direction formed of a first material, said rigid shield having a wall including an inner surface and an outer surface, B. implementing a flexible shield formed of a second material different from the first material onto the rigid shield, said flexible shield comprising an outer layer configured to cover at least part of the rigid shield outer surface and an inner layer being capable of receiving in a sealing way at least a part of the hub portion of the medical injection device, and configured to cover at least partly the inner surface of the rigid shield, and C. inserting a septum within the rigid shield, said septum being formed of a third material different from the said first and second materials, said septum being configured to be at least partly in contact with the inner surface of the rigid shield.

13. The method according to claim 12, wherein in step A), the rigid shield is injection molded, and wherein the method comprises a step D) performed before step A) wherein a wireless transmitter is disposed in a mold before the injection molding of the rigid shield.

14. The method according to claim 12, wherein in step A), the rigid shield is injection molded, and wherein the method comprises a step D) performed after step A) wherein a wireless transmitter is overmolded on the outer surface of the wall of the rigid shield before being surrounded by the outer layer of the flexible shield.

15. The method according to claim 12, wherein in step B), the flexible shield is implemented on the rigid shield by overmolding.

* * * * *